United States Patent [19]

Edgington et al.

[11] Patent Number: 5,023,236
[45] Date of Patent: Jun. 11, 1991

[54] FACTOR VII/VIIA ACTIVE SITE INHIBITORS

[75] Inventors: T. Scott Edgington, La Jolla; Michael G. Pepe, San Diego, both of Calif.

[73] Assignee: Corvas, Inc., San Diego, Calif.

[21] Appl. No.: 320,559

[22] Filed: Mar. 13, 1989

Related U.S. Application Data

[63] Continuation-in-part of Ser. No. 178,495, Apr. 7, 1988, abandoned.

[51] Int. Cl.5 .................... A61K 37/02; C07K 5/08
[52] U.S. Cl. ..................................... 514/18; 530/331
[58] Field of Search ........................... 530/331; 514/18

[56] References Cited

U.S. PATENT DOCUMENTS

| | | | |
|---|---|---|---|
| 4,275,153 | 6/1981 | Gargiulo | 530/331 |
| 4,399,065 | 8/1983 | Bajusz et al. | 530/331 |
| 4,622,389 | 11/1986 | Nagasawa et al. | 530/331 |
| 4,636,492 | 1/1987 | Kettner et al. | 530/331 |
| 4,713,369 | 12/1987 | Stuber | 530/331 |

FOREIGN PATENT DOCUMENTS 0293881 1/1988 European Pat. Off. .

OTHER PUBLICATIONS

Emerson, Y. and Gentry, R. (1986) Biochem. 25:4020–4033.
Schechter, I. and Berger, A. (1967) Biochem. Biophys. Res. Comm. 27:157–162.
Power, J. C. et al., (1977) Biochim. Biophys. acta 485:156–166.
Imperiali, B. and Abeles, R. H. (1986) Biochem. 25:3760–3767.
Yoshimura, T. et al. (1982) J. Biol. Chem. 257:5077–5084.
Matteson, D. S. et al. (1981) J. Am. Chem. Soc. 103:5241–5242.
Kettner, C. A. and Shenvi, A. B. (1984) J. Biol. Chem. 259:15106–15114.
Jacobsen, N. E. and Barlett, P. A. (1981) J. Am. Chem. Soc. 103:654–657.
Fung, M. R. et al. (1985) Proc. Natl. Acad. Sci. 82:3591–3595.
Kawabata, S.-i. et al. (1988) Eur. J. Biochem. 172:17–25.
Harmon, J. T. and jamieson, G. A. (1986) J. Biol. Chem. 261:15928–15933.
Mohler, M. A. et al., (1986) Thromb. Haemost. 56:160–164.

*Primary Examiner*—Lester L. Lee
*Attorney, Agent, or Firm*—Greenlee and Associates

[57] ABSTRACT

The invention includes a class of compounds that inhibit the specific proteolytic activity of the bimolecular complex 1[TF:VII/VIIa] that initiates the blood coagulation systems. Both reversible and irreversible inhibitors are disclosed.

The invention encompasses the use of inhibitors of the active site of the factor VII and VIIa component of [TF:VII/VIIa] as diagnostic reagents, as analytical reagents, and as therapeutic drugs.

The invention includes the compounds based on the following general formula for both reversible and irreversible selective inhibition of [TF:VII/VIIa].

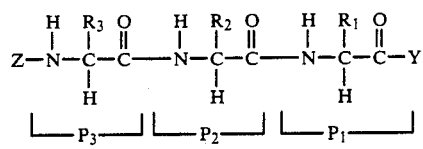

58 Claims, No Drawings

FACTOR VII/VIIA ACTIVE SITE INHIBITORS

This application is a continuation-in-part of co-pending application Ser. No. 178,495, filed Apr. 7, 1988 and now abandoned, which is incorporated herein by reference.

FIELD OF THE INVENTION

This invention relates to the field of blood coagulation and encompasses peptidyl molecules that are inhibitors of the extrinsic coagulation factor VII/VIIa that is associated with tissue factor.

BACKGROUND OF THE INVENTION

The major established physiologic mechanism for cellular initiation of the human extrinsic coagulation protease cascade is attributed to expression of the glycoprotein Tissue Factor (TF) (Morrisey et al. (1987) Cell 50:129-135) on the surface of cells (Broze (1982) J. Clin. Invest. 70:526-535); Ploplis et al. (1987) J. Biol. Chem. 262:9503-9508). TF is a cell surface receptor that specifically binds plasma factor VII, or its more active two chain derivative VIIa, at a 1:1 ratio to form the binary complex [TF:VII] or [TF:VIIa], hereafter referred to as [TF:VII/VIIa]. The catalytically active moiety is termed herein factor VII/VIIa and possesses esterase activity (Zur and Nemerson (1978) J. Biol. Chem. 253:2203-2209) even in the absence of binding to TF. The [TF:VII/VIIa] binary complex is proteolytically active (Nemerson and Gentry (1986) Biochem. 25:4020-4033) due to substrate association with the functional serine protease type active site of the factor VII/VIIa of the complex. [TF: VII/VIIa] acts as a protease that is highly specific for two other proteins, the serine protease zymogens, factor X (Silverberg et al. (1977) J. Biol. Chem. 252:8481-8488) and factor IX (Osterud et al. (1977) Proc. Natl. Acad. Sci. 74:5260-5264), both of which are in turn rendered active as proteases by the action of the serine type catalytic site of factor VII/VIIa when organized into the bimolecular complex [TF:VII/VIIa]. Due to the specificity of [TF:VII/VIIa] for factor IX, [TF:VII/VIIa] is also capable of activating the intrinsic coagulation protease cascade on some cells, for example on endothelial cells of the vasculature (Stern et al. (1984) Proc. Natl. Acad. Sci. 81:913-917). Initiation of one or both coagulation protease cascades on the surface of intravascular cells is a critically important pathogenetic basis for initiation of thrombosis (Niemetz and Fani (1973) Blood 42:47-59; Stern et al. (1984) supra) and disseminated intravascular coagulation (Niemetz and Fani (1971) Nature New Biol. 232:247-248). Both coagulation protease cascades play a role in the inflammatory response to viruses and immune mediated diseases (Levy et al. (1981) J. Exp. Med. 254:1150-1163).

There are no prior established inhibitors specific for factor VII/VIIa when free or part of the [TF:VII/VIIa] binary complex. There are no known specific inhibitors of this "initiation" of the coagulation protease cascades by the proteolytically active [TF:VII/VIIa] bimolecular complex.

The present invention, providing the ability to specifically inhibit proteolytic activity of the [TF:VII/-VIIa] binary complex, represents a significant and useful advance. Compounds of the invention permit diagnostic evaluation of the molecular basis of cellular activation of coagulation in the thrombotic, inflammatory and related intravascular coagulation and immunologic diseases. Second, such compounds permit analysis for the development of drugs based on the activity of the [TF:VII/VIIa] complex. Third, such compounds represent a new class of anti-thrombotic and anti-inflammatory drugs.

The usefulness of the class of compounds described in this invention derives from the ability of these compounds to function a active site inhibitors specific for factor VII/VIIa. Both reversible and irreversible inhibitors are described. The irreversible inhibitors are capable of efficient inhibition and are selective for factor VII/VIIa when active by association with tissue factor (TF)in the proteolytically active binary complex [TF:VII/VIIa].

The compounds of the invention are used as analytical reagents and therapeutic agents to specifically inhibit the initiation of the coagulation protease cascades by [TF:VII/VIIa]. The compounds also permit accurate in vitro and ex vivo determination whether or not activation of coagulation is attributable to the binary complex [TF:VII/VIIa]. The compounds are used as therapeutic drugs in vivo to inhibit the initiation of the coagulation system which is one of the pathogenetic mechanisms required for thrombus formation and the thrombotic and related diseases, disseminated intravascular coagulation associated with septic shock and other disease processes, and certain inflammatory conditions associated with excessive activation of coagulation in the tissues.

SUMMARY OF INVENTION

This invention includes peptides and peptide derivatives that specifically inhibit the proteolytic active site of the serine protease coagulation factor VII/VIIa when active as a result of association with its high affinity cellular receptor TF.

Compounds of formula I are inhibitors of factor VII/VIIa in the [TF:VII/VIIa] complex described in this invention:

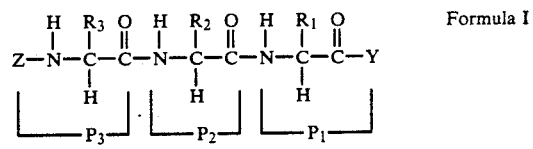

Formula I wherein $R_1$ is an arginine side chain $-[CH_2]_3-NH-CNHNH_2$; $R_2$ is a threonine side chain $-CHOH-CH_3$, serine side chain $-CH_2OH$ or proline side chain $-(CH_2)_3-$ such that $P_2$ is proline except when $P_3$ is D-phenylalanine; wherein $R_3$ is an amino acid side chain of asparagine $-CH_2-CONH_2$, or aspartic acid $-CH_2-COO^-$, or histidine

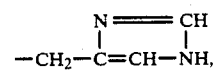

leucine $-CH_2-CH-[CH_3]_2$, glutamine $-[CH_2]_2-CONH_2$, threonine $-CHOH-CH_3$ or phenylalanine

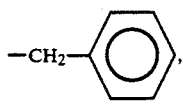

so oriented that $P_3$ is either the D or L isomer. Y is hydroxy or a straight or branched alkoxy group with one to four carbon atoms, such as methoxy, ethoxy, n-propoxy, isopropoxy, n-butoxy and the like as well as benzyloxy, or $NA_1A_2$ wherein each of $A_1$ and $A_2$ is H or a lower alkyl group having one to four carbon atoms, such as methyl, ethyl, n-propyl, isopropyl, and $A_1$ and $A_2$ are the same or different, or a chloromethyl or a fluoromethyl. Z is usually an H but may be substituted by a variety of groups including a straight, branched alkyl or CH or CHO ring group or CHO having from one to six carbon atoms, for example, methyl, ethyl, n-propyl or isopropyl, n-butyl, tert-butyl, benzyl and the like, or more complex chemical derivatives such as formyl, acetyl, dansyl (5-dimethylaminonaphthalenesulfonyl), tosyl (p-toluenesulfonyl) or Boc (tert-butyloxycarbonyl) groups. Less advantageous derivatives include the general compound without the $P_3$ region and with Z bonded to the N of $P_2$.

Compounds of the above general formula are irreversible o tight inhibitors of factors VII/VIIa in the binary [TF:VII/VIIa] complex when Y is a reactive group capable of forming either a covalent or a tight bond with a reactive site residue in the enzyme such as with the reactive serine or histidine in the charge relay system of serine proteases. Irreversible inhibitors are exemplified by compounds of the above general formula when Y is a chloromethyl or fluoromethyl.

Such irreversible or tight inhibitors are otherwise similar in respect to groups Z, $R_1$, $R_2$, $R_3$, as described above for reversible inhibitors.

Pharmaceutically acceptable salts of the compounds of the general formula I are also included in the scope of the present invention as well as chemical derivatives of the $P_1$ arginine, $P_2$ threonine or $P_3$ side chains. The compounds of formula I and pharmaceutically acceptable salts thereof are useful in the treatment of thrombosis, disseminated intravascular coagulation, septic shock, inflammation of the cellular immune type diseases such as arthritis, and sarcoidosis.

DETAILED DESCRIPTION OF INVENTION

The compounds of the invention are believed to act as tripeptide analogues of the physiological substrates of [TF:VII/VIIa], which are thought to bind the $P_1$–$P_3$ sites (per nomenclature of Schechter and Berger (1967) Biochem. Biophys. Res. Comm. 27:157–162) of the active enzyme form of factor VII or derivative VIIa only when they are associated with their high affinity cellular receptor TF in the binary complex [TF:VII/VIIa]. The amino acid residues or analogues represented by $P_1$, $P_2$ and $P_3$ of Formula I are thought to correspond to $P_1$, $P_2$ and $P_3$, respectively, of the substrate of a serine protease type of enzyme.

Substituent $R_1$ is preferably the side chain of arginine or a reactive derivative that preferably conveys on the local structure and particularly the

the geometry and reactivity of a transition state analogue. For reversible inhibitors the amino acid side chain of arginine is preferably used at $R_1$.

$R_2$ is preferably the side chain of a threonine residue.

$R_3$ may be occupied by a variety of structures which are consistent with the highly selective specificity for substrates of [TF:VII/VIIa] even though such structures may not exist in natural substrates and are not obvious. Preferable $R_3$ structures are exemplified by amino acid residue side chains listed in Table 1. The most effective are listed by relative inhibitory activity.

TABLE I

| Relative Efficacy of $P_3$ Substituents | |
|---|---|
| Amino Acid Side Chain | Relative potency $K_i 5$ (MU) |
| Asparaginyl | 6.7 |
| Histidyl | 6.2 |
| Aspartyl | 4.8 |
| Leucyl | 4.5 |
| Threonyl | 2.6 |
| Glutaminyl | 2.5 |
| None | 2.0 |
| Other | 0 |

Relative potency is expressed as megaunits (MU), where one unit is equal to the inverse of the molar concentration at 5% inhibition of factor X activation. Quantitation of inhibition of factor VII/VIIa in the binary complex with tissue factor was performed in a linked enzyme chromogenic assay using factor X, purified as described by Schwartz, B. S. et al. (1981) J. Clin. Invest. 67:1650, and the chromogenic substrate S-2222 (Helena Labs, Beaumont, Texa s). Briefly, the peptides were preincubated with purified human factor VII (1 nM), purified as described by Fair, D. S. (1983) Blood 62:784–791, in a total volume of 75 μl, after 30 min incubation at room temperature 25 μl of 20 mM $CaCl_2$, 1 × $10^5$ TF positive human bladder carcinoma derived J82 cells (available from American Type Culture Collection, Rockville, Maryland, under Accession No. ATCC HTB1), 25 μl of purified human factor human factor X (100 ηM) in 50 μl of TRIS buffered saline and 50 μl of 2 mM S-2222 was added. The use of J82 cells is an important feature of these in vitro assays because they produce significant levels of TF for the formation of active TF:VII/VIIa. The rate of conversion of factor X to Xa was monitored kinetically by determination of the chromogenic product of S-2222 by absorbance at 405 nm.

Other substitutions, including the alanyl, prolyl, glycyl, arginyl, seryl, phenylalanyl, tryptophanyl, valyl, isoleucyl, glutamyl, tyrosyl, cysteinyl or methionyl side chains as $R_3$, actively negate the weak inhibitory activity of the dipeptide threonyl-arginine or derivatives resulting in inactive compounds.

Substituent $R_3$ of Formula I is most preferably based on the structure of the amino acid side chains of asparagine or histidine, though less preferred forms include structures based on the amino acid side chains of aspartic acid and leucine which are functional inhibitors and structures based on threonine and glutamine side chains are still less favored as reversible inhibitors. The dipeptide threonyl-arginine possesses slight activity which is improved by addition of $P_3$ with appropriate substituents. The amino terminal Z group is preferably an H or various other moieties described in the art to increase reactivity through hydrogen bonding or other substitution to facilitate covalent bonding.

A relatively effective form of the reversible inhibitor is L-asparaginyl-L-threonyl-L-arginine (L-Asn-L-Thr-L-Arg) as in general Formula II and Example 1.

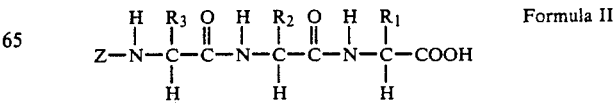

wherein Z is H, wherein $R_3$ is the L-asparaginyl side chain $-CH_2-CONH_2$; wherein $R_2$ is the L-threonyl side chain $-CHOH-CH_3$, and wherein $R_1$ is the L-arginyl side chain $-[CH_2]_3-NH-CNHNH_2$. The D-isomer of the individual amino acids making up the peptidyl moiety may also be employed. Unless otherwise specified, the L-form of $P_1$, $P_2$ and $P_3$ is employed, herein.

Irreversible or tight-binding inhibitors are derivatives of the reversible inhibitors, modified to incorporate a reactive group at

capable of forming a covalent or very tight bond with the active site of the catalytic domain of factor VII/-VIIa resulting in a stable inhibitor-enzyme complex. Well-known examples of irreversible inhibitors include: 1) peptide chloromethyl ketones (CMK) (Powers et al. (1977) Biochim. Biophys. Acta 485:156-166; and 2) peptide fluoromethyl ketone (FMK) (Imperiali and Abeles (1986) Biochem. 25:3760-3767); HN-arylsulfonyl fluorides (Yoshimura et al. (1982) J. Biol. Chem. 257:5077-5084); and of tight-binding inhibitors include: 1) peptide boronic acids (Matteson et al. (1981) J. Am. Chem. Soc. 103:5241-5242; Kettner and Shenvi (1984).

Chloromethyl ketone derivatives have been analyzed for inhibition of the specific proteolytic activity of [TF:VII/VIIa] on the surface of TF positive assay cells. The relative inhibitory potency is substantially enhanced as indicated in Table 2.

TABLE 2

Comparison of Inhibitory Activity of Chloromethyl Ketone Analogues

| Peptidyl Analogue | Peptide ($K_i5$) | Peptidyl-CMK ($K_i5$) | $K_i50$ |
|---|---|---|---|
| H—L—His—L—Thr—L—Arg | 6.2 MU | 54.0 MU | 120 μM |
| H—L—Leu—L—Thr—L—Arg | 4.5 MU | 67.5 MU | 95 μM |

The inhibitory potency of the peptides and peptidyl chloromethyl ketones (CMK) was assayed as described for Table 1. $K_i5$ is given in MU (legend Table 1). $K_i50$ is given in conventional molar terms, i.e. concentration required for 50% inhibition of the rate of factor X activation.

A preferred form of the irreversible inhibitor is H-L-leucyl-L-threonyl-L-arginyl chloromethyl ketone (L-Leu-L-Thr-L-Arg-CMK) as in the general Formula III and profiled in Tables 2 and 3.

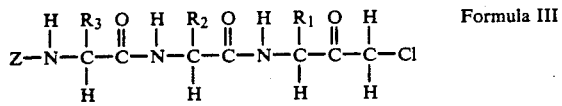

Formula III wherein Z is H, wherein $R_3$ is $-CH_2-CH[CH_3]_2$; wherein $R_2$ is $-CHOH-CH_3$, wherein $R_1$ is $-CH_2-CH_2-CH_2-NH-CNHNH_2$.

The leucyl residue in the $P_3$ position may be chemically modified, for example, to contain an acetyl or tosyl group without significant loss of biological activity as illustrated in Table 3. (However, modification of the $P_3$ leucine residue to include a dansyl group in the Z position results in decreased biological activity.) Moreover, in the preferred L-Leu-L-Thr-L-Arg-CMK inhibitor compound, the amino acid residue at the $P_2$ position can be substituted with serine or proline without significant loss of inhibitory activity as shown in Table 3.

A more preferred form of the irreversible inhibitor is D-leucyl-L-threonyl-L-arginyl chloromethyl ketone (D-Leu-L-Thr-L-Arg-CMK) wherein the amino acid residue at the $P_3$ position is the D-isomer of leucine. The inhibitory activity of the tripeptidyl-CMK is significantly enhanced (see Table 3) when the $P_3$ position contains D-leucine instead of L-leucine. When D-leucine is replaced with D-phenylalanine in the $P_3$ position, the activity decreases by more than 50% (Table 3).

TABLE 3

Inhibitory Activities of Some Peptidyl Chloromethyl Ketones

| Peptidyl—CMK | $K_i5$ |
|---|---|
| L—Leu—L—Thr—L—Arg—CMK | 68 MU |
| Ac—L—Leu—L—Thr—L—Arg—CMK | 60 |
| Tosyl—L—Leu—L—Thr—L—Arg—CMK | 60 |
| Dansyl—L—Leu—L—Thr—L—Arg—CMK | 35 |
| D—Leu—L—Thr—L—Arg—CMK | 100 |
| L—Leu—L—Ser—L—Arg—CM | 60 |
| L—Leu—L—Pro—L—Arg—CMK | 60 |
| L—His—L—Thr—L—Arg—CMK | 54 |
| L—Asn—L—Thr—L—Arg—CMK | 44 |
| L—Asn—L—Ser—L—Arg—CMK | 60 |
| L—Asp—L—Thr—L—Arg—CMK | 60 |
| D—Phe—L—Thr—L—Arg—CMK | 42 |

The inhibitory activity of the peptidyl chloromethyl ketones was assayed as described for Table 1. $K_i5$ is given in MU (legend, Table 1).
Ac = acetyl
Tosyl = p-toluenesulfonyl
Dansyl = 5-dimethylaminonaphthalenesulfonyl Compounds representative of this invention have been synthesized and demonstrated to be active in inhibiting the activation of factor X by human cells expressing the TF molecule that have been provided with factor VII to form the binary proteolytic activation complex [TF:VII/VIIa]. Inhibition by the compounds of this invention of the proteolytic activity of [TF:VII/VIIa] on factor X was analyzed by a chromogenic assay in which the substrate S-2222 is cleaved by the generated factor Xa. Inhibition of the clotting of normal human plasma was also demonstrated, assayed after addition of TF positive cells, inhibitor compound and calcium. Analyses included the absence of effect of all such compounds on factor Xa, an enzyme closely homologous to factor VII and VIIa. None of the compounds exhibited any inhibitory effect on the cleavage of S-2222 by factor Xa.

Halomethyl ketone derivatives as irreversible inhibitors are as described above for chloromethyl ketone derivatives in respect to substituted groups with the exception that the halomethyl group at Y preferably contains an F in place of Cl.

Illustrative examples of pharmaceutically acceptable salts of the compounds include non-toxic salts formed with organic or inorganic acids or bases, for example salts of alkali metals such as sodium, potassium, or lithium; salts of alkaline metals such as calcium or magnesium; salts of organic amines such as cyclohexylamine, ethylamine, pyridine, ethanolamine or piperazine; and salts formed with anions, such as chloride, fluoride, bromide, succinate or acetate salts. The salts are prepared by conventional means.

The compounds of this invention based on general formula I are inhibitors of the catalytic site of factor VII/VIIa in the proteolytic [TF:VII/VIIa] binary complex as demonstrated by their ability to inhibit factor Xa generation assayed as described in the footnote to Table 1. As a result of their inhibitory activity these compounds and their salt forms are useful in the treatment of cellular activation of coagulation in thrombosis, disseminated intravascular coagulation, septic shock, cellular immune responses, sarcoidosis, and related diseases where the coagulation pathways are activated as part of the inflammatory response.

In practicing the present invention the compounds of Formula I and pharmaceutically acceptable salts thereof may be used alone or mixed with a pharmaceutically acceptable carrier. Such compounds or salts can be administered to patients parenterally, for example subcutaneously, intravenously or intraperitoneally. Such compounds can be administered by intranasal instillation or by application to mucous membranes such as those of the sublingual region of the mouth or the nasal or bronchial mucosa as a spray, dry particle suspension or solution in water or saline solution.

The data shown herein demonstrate the activity of representative compounds of the invention for inhibiting the proteolytic activity of [TF:VII/VIIa] which results from binding and inhibition of the active catalytic site of the factor VII/VIIa moiety of [TF:VII/VIIa] in an in vitro assay of proteolytic activations of factor X and in a plasma clotting-time assay. Conditions for treatment of patients can be optimized following further quantitation of activity ex vivo and in laboratory animals, according to principles well-known in the art. The development of pharmaceutically-acceptable carriers, diluents and vehicles for administration of the inhibitor in an active, physiologically-compatible form follows well-known principles. For practical purposes, inhibition dose should be less than 300μM, and preferably less than 30μM, in the subject's blood, which in turn means that a pharmaceutically effective inhibitor must have a $K_i50$ of less than 300 μM or a $K_i5$ equal to or greater than 2.0. Furthermore, the inhibitor should be specific for [TF:VII/VIIa]. Many nonspecific serine protease inhibitors are known in the art. These have no relevance herein, since they inhibit many enzymes and can be toxic at effective doses. Inhibitors of the present invention are highly selective for the factor VII/VIIa moiety of [TF:VII/VIIa]. They have no inhibitory effect, for example at doses as high as 300 μM, on factor IXa or thrombin, which are homologous serine type proteases. Preferred compounds of the present invention are those which have high $K_i5$ (MU) and low $K_i50$ (μM) values, since these can be effective at lower dosage, reducing the likelihood of side effects.

This invention combines the specific teachings of the present disclosure with a variety of techniques and expedients known in the art. The choice of expedients depends on variables such as the selection of peptide length, choice of reactive group to define binding at the active site, the extent of modification within each amino acid residue, manipulation of amino acid sequences affecting stabilization/destabilization at the active site, insertion of amino acids that reflect the proper geometry at $P_2$ and $P_3$ sites, addition or modification of chemical ligands to allow future exploitation of binding affinities, and the like. As novel, natural and synthetic peptide substrate and inhibitor molecules are discovered and evaluated, and as sequences and ligands responsible for enhanced binding and reactivity at the active site are elucidated, those of ordinary skill in the art will be able to select among those elements to produce "improved" synthetic peptidyl analogs having desired biological activities. The fundamental aspect of the present invention is the ability to utilize novel peptidyl compounds to inhibit the proteolytic activity of [TF:VII/VIIa] by designing peptidyl compounds so that they bind selectively and with enhanced affinity to the catalytic site of factor VII/VIIa.

EXAMPLES

The following Examples are presented as illustrations of embodiments of the present invention. They do not limit the scope of this invention, which is determined by the claims.

The peptidyl inhibitor compounds of this invention can be readily synthesized using any of a number of synthetic chemical approaches used routinely in the art (Fridkin and Patchornik (1974) Ann. Rev. Biochem. 43:419-443; Kent (1988) Ann. Rev. Biochem. 57:957-990). The preferred strategies used for the synthesis of peptides are those based on (a) synthesis in homogeneous (solution) or heterogeneous (liquid/solid-phase) systems, and (b) methods involving fragment or stepwise condensation reactions (Bodansky and Ondetti (1965) Peptide Synthesis, New York, Interscience). The synthesis of halomethyl ketone and related derivatives (e.g. of desired peptides can be readily accomplished by methods familiar to those of ordinary skill in the art (see Powers and Tuhy (1973) Biochemistry 12:4767-4774; Kurachi et al. (1973) Biochemistry 12:771-777; Powers et al. (1976) Biochim. Biophys. Acta 480:246-261; Imperiali and Abeles (1986) Biochemistry 25:3760-3767; Imperiali and Abeles (1986) Tetrahedron Lett. 27:135.

EXAMPLE 1

Synthesis of H-L-Asn-L-Thr-L-Arg

Representative solid phase synthesis of this compound was performed on an Applied Biosystems Model 430A peptide synthesizer using standard manufacturer protocols and the t-Boc protected derivatives N-α-Boc-L-Asparagine, N-Boc-O-Bzl-L-Threonine, and tosyl-L-Arginine derivatized PAM resin as the support. The tripeptide is deprotected and cleaved from the PAM support by standard protocols and reagents including HF cleavage [anisole:resin:HF (1:1:10)] for 60 min at 0° C. The product is purified on a Vydac C-18 column eluted with 10-40% (v/v) acetonitrile in $H_2O$ containing 0.1% (v/v) TFA gradient, dried under vacuo. The product is used for analysis by dissolving it in water or desired aqueous solution.

EXAMPLE 2

Synthesis of H-L-Asp-L-Thr-L-Arg

Synthesis of this analogue is performed in a satisfactory fashion on an Applied Biosystems Model 430A peptide synthesizer using standard protocols for asymmetric anhydride formation for coupling to a PAM resin cartridge derivatized with Tosyl-L-Arginine in which first N-Boc-O-Bzl-L-Threonine is coupled, the t-Boc removed and then N-Boc-L-Aspartic acid-β-Benzyl ester is activated to an asymmetric anhydride and coupled to the threonyl group. The tripeptide is deprotected and cleaved from the PAM resin using the standard HF protocol and prepared as above (Example 1).

EXAMPLE 3

Synthesis of H-L-His-L-Thr-L-Arg

The peptide was synthesized essentially as described in Example 2, substituting N-α-Boc-N-im-Cbz-L-Histidine for the final amino acid coupling reaction.

EXAMPLE 4

Synthesis of H-L-Leu-L-Thr-L-Arg

Synthesis was performed essentially as described in Example 2, except for the use of N-Boc-L-Leucine in the final amino acid coupling reaction.

EXAMPLE 5

Synthesis of H-L-Thr-L-Thr-L-Arg

Synthesis was performed essentially as described in Example 2, substituting N-Boc-O-Bzl-L-Threonine in the final amino acid coupling reaction.

EXAMPLE 6

Synthesis of H-L-Gln-L-Thr-L-Arg

Synthesis was performed essentially as described in Example 1 substituting N-α-Boc-L-glutamine in the final amino acid coupling reaction.

EXAMPLE 7

Synthesis of H-L-Thr-L-Arg

Synthesis was performed essentially as described in Example 1, omitting the final amino acid coupling reaction.

EXAMPLE 8

Synthesis of H-L-Asn-L-Thr-L-Arg-CMK (a) Peptide Synthesis Using Solution Phase Technique. This method is the more preferred and can be carried out as follows.

Preparation of H-Arg(NO$_2$)CH$_2$CL.HCl. Boc-L-Arg(NO$_2$)OH (5.00 g, 15.6 mmol) was dissolved in tetrahydrofuran (THF) (200 ml) and treated with isobutyl chloroformate (2.06 g, 15.6 mmol) in the presence of N-methylmorpholine (1.72 ml, 15.6 mmol) for 10 min at 0° C. The mixed anhydride preparation was filtered, and the filtrate was added to ethereal diazomethane [120 ml prepared from Diazald (5.4 g, 25 mmol)] over a period of 5 min. After the reaction was stirred at 0° C. for 45 min, acetic acid (0.5 ml) was added to quench the excess diazomethane. The product crystallized from the reaction mixture. The solvent was removed, and the residue was diluted with chloroform (25 ml). The crystalline product, Boc-L-Arg(NO$_2$)CHN$_2$, was filtered and dried in vacuo. Boc-L-Arg(NO$_2$)CHN$_2$ (3.97 g, 11.5 mmol) was dissolved in ethanol (23 ml) and cooled to 0° C. HCl (12.5 ml of a 10% solution in ethanol) was added dropwise over a period of 20 min. After the reaction mixture was stirred at room temperature (RT) for 1 hr, it was poured into diethyl ether (400 ml). The solution was allowed to stand for 2 hr at 5° C., filtered under N$_2$, and dried in a vacuum desiccator to afford 1.72 g H-L-Arg(NO$_2$)CH$_2$Cl.HCl as a white powder. The product was characterized by 360 MHz $^1$H NMR.

Preparation of Cbz-L-Asn-L-(O-t-butyl)-ThrOH. To an ice cooled solution of Cbz-AsnOH (2.66 g, 0.01 mol) and N-hydroxybenzotriazole (1.53 g, 0.01 mol) in THF (40 ml) were added successively (O-t-butyl)-threonine methyl ester HCl (2.26 g, 0.01 mol), N-methylmorpholine (1.10 ml, 0.01 mol) and dicyclohexylcarbodiimide (DCC) (2.16 g, 0.01 mol) in THF (5 ml). After the addition was complete, the solution was stirred at 0° C. for 1 hr and at RT for 16 hr. The reaction mixture was cooled with an ice bath, and the excess DCC was quenched with acetic acid (0.50 ml). After 1 hr, the solution was filtered, washing the dicyclohexylurea (DCU) precipitate with ethyl acetate (25 ml). The solvent was removed from the filtrate, and the residue was dissolved in ethyl acetate (25 ml). After the solution was allowed to stand for 3h at 5° C., the remaining DCU precipitate was removed by filtration. The filtrate was diluted to 100 ml with ethyl acetate, washed with 10% citric acid, water, saturated NaHCO$_3$ and brine (saturated NaCl solution) (15 ml each), dried over MgSO$_4$, filtered, and the solvent was removed in vacuo to afford Cbz-L-Asn-L-(O-t-butyl)-ThrOMe (4.02 g, 89%). To an ice cooled solution of Cbz-L-Asn-L-(O-t-butyl)-ThrOMe (4.02 g, 8.9 mmol) in methanol/dioxane (1:1)(25 ml) was added NaOH (12 ml of a 1.0 N solution, 12 mmol). The solution was stirred at RT for 3 hr. The methanol and dioxane were removed under reduced pressure. The aqueous solution was diluted with H$_2$O (50 ml), washed with ethyl acetate two times (25 ml each), and acidified to pH 2 with 1M NaHSO$_4$. The aqueous layer was extracted with ethyl acetate 2 times (50 ml each). The combined organic layers were washed with brine three time (10 ml each), dried over MgSO$_4$, and the solvent was removed in vacuo to yield Cbz-L-Asn-L-(O-t-butyl)-ThrOH (2.14 g, 55%). The product was characterized by 60 MHz $^1$H NMR.

Preparation of H-Asn-Thr-Arg-CMK. The preformed protected dipeptide, Cbz-L-Asn-L-(O-t-butyl)-ThrOH (0.88 g, 2.0 mmol), was allowed to react with isobutyl chloroformate (0.29 ml, 2.1 mmol), in the presence of N-methylmorpholine (0.24 ml. 2.1 mmol) at 0° C. for 20 min. A solution of H-L-Arg(NO$_2$)CH$_2$Cl.HCl (0.60 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with H$_2$O and brine (25 ml each), extracted twice with ethyl acetate (25 ml each). The combined organic layers were washed with 10% citric acid, saturated NaHCO$_3$ and brine (15 ml each), dried over MgSO$_4$, and the solvent was removed in vacuo to give Cbz-L-Asn-L-(O-t-butyl)-Thr-L-Arg(NO$_2$)CH$_2$Cl. The product was treated with HF (7 ml) and anisole (0.5 ml) at 0° C. for 20 min. After the HF was removed, the residue was diluted with cold H$_2$O and washed with diethyl ether two times (5 ml each). The organic volatiles were removed under reduced pressure before lyophilizing the crude H-L-Asn-L-Thr-L-Arg-CMK.2HF to a powder. A crude purification of the material was accomplished on a Sephadex SP-C25 (H+form) column using 0–1.0N HCl stepwise gradient which yielded 124 mg H-L-Asn-L-Arg-CMK.2HCl. The product was further purified on a Supelco LCNH$_2$ column eluted with a 10–50% (v/v) hexane/isopropanol (10% methanol) gradient, and dried in vacuo. The product was characterized by 360 MHz $^1$H NMR. The product was dissolved in water, methanol, or suitable aqueous solutions for analysis or other uses.

(b) Peptide Synthesis Using Solid Phase Technique.

Preparation of H-Arg(NO$_2$)CH$_2$Cl.HCl. Boc Arg-(NO$_2$)OH (5.0 g, 15.6 mmol) was dissolved in 60 ml of tetrahydrofuran (THF) and was allowed to react with isobutyl chloroformate (2.06 ml, 15.6 mmol) in the presence of N-methylmorpholine (1.72 ml, 15.6 mmol) for 10 min at −20° C. The mixed anhydride preparation was filtered, and the filtrate was added to 120 ml of ethereal diazomethane. After stirring the reaction solution for 30 min at 0° C., 80 ml of ether was added. The product crystallized from the reaction solution in the cold. The Boc-Arg(HO$_2$)CHNH$_2$ product was dissolved in a minimum volume of THF and was allowed to react with ethanol HCl (20 mmol) at room temperature until nitrogen evolution ceased.

Preparation of H-Asn-Thr-Arg-CMK. The preformed peptide Boc-Asn-O-Bzl-Thr-OH (1 mmol), which was satisfactorily synthesized by any of methods well-known to the art and satisfactorily on an Applied Biosystems Model 430A peptide synthesizer by standard instrument protocols (See: Mergler et al. (1988) *Peptides, Chemistry and Biology*. Proc. of Tenth American Peptide Symposium, St. Louis, G. R. Marshall (ed.) ESCOM Leiden, p. 259), was allowed to react with N-methylmorpholine (1 mmol) in 5 ml of THF for 10 min at −20° C. H-Arg(NO$_2$)CH$_2$Cl.HCl (1 mmol) dissolved in 5 ml of cold N,N-dimethylformamide was added to the mixed anhydride preparation. After 15 min was added cold THF (20 ml) containing triethylamine (1 mmol). After stirring for 1 hr at −20° C. and 2 hr at room temperature, the reaction mixture was filtered, the filtrate was suspended in ethyl acetate and the ethyl acetate layer was washed with water before being evaporated to dryness. The crude product was deprotected by HF cleavage [anisole:crude product:HF (1:1:10)] for 60 min at 0° C. and an aqueous suspension of the crude product was washed 3 times with ether followed by three washes with chloroform. The combined organic layers were washed sequentially with 0.1N HCl, H$_2$O, 1M K$_2$CO$_3$ and saturated NaCl, dried over MgSO$_4$ and the solvent was removed in vacuo. The product was purified on a Vydac C-18 column eluted with a 10–40% (v/v) acetonitrile in H$_2$O containing 0.1% (v/v) TFA gradient, and dried under vacuo. The product was dissolved in water or suitable aqueous solution for analysis or other uses.

EXAMPLE 9

Synthesis of H-L-Asp-L-Thr-L-Arg-CMK (a) Peptide Synthesis Using Solution Phase Technique.

Preparation of H-L-Arg(NO$_2$)CH$_2$Cl.HCl. Boc-L-Arg(NO$_2$)OH was first converted to Boc-L-Arg(NO$_2$)CNH$_2$ and then to H-L-Arg(NO$_2$)CH$_2$Cl.HCl using the procedure exactly as described in Example 8.

Preparation of N-α-cbz-β-t-butyl ester-L-Asp-L-(O-t-butyl)-ThrOH. N-α-cbz-β-t-butyl ester-L-AspOH (0.01 mol) was coupled to L-(O-t-butyl)-ThrOMe (0.01 mol) to form N-α-cbz-β-t-butyl ester-L-Asp-L-(O-t-butyl)-ThrOMe which was deesterified to yield N-α-cbz-β-t-butyl ester-L-Asp-L-(O-t-butyl)-ThrOH, using the procedure outlined in Example 8 for the preparation of Cbz-L-Asn-L-(O-t-butyl)-ThrOH.

Preparation of H-L-Asp-L-Thr-L-Arg-CMK. The preformed protected dipeptide, N-α-cbz-β-t-butyl ester -L-Asp-L(O-t-butyl)-ThrOH, (2.0 mmol) was allowed to react with isobutylchloroformate (2.1 mmol) in the presence of N-methylmorpholine (2.1 mmol) at 0° C. for 20 min. A solution of H-L-Arg(NO$_2$)CH$_2$Cl.HCl (2.0 mmol) in dimethylformamide (4 ml) was added dropwise. After stirring for 20 min at 0° C., N-methylmorpholine (2.0 mmol) in THF was added. The resulting solution was stirred at 0° C. for an additional 40 min, then at RT for 1 hr. The reaction mixture was diluted with H$_2$O and brine (25 ml each), extracted twice with ethyl acetate (25 ml each). The combined organic layers were washed with 10% citric acid, saturated NaHCO$_3$ and brine (15 ml each), dried over MgSO$_4$, and the solvent was removed in vacuo to give N-α-cbz-β-t-butyl ester-L-Asp-L-(O-t-butyl)-Thr-L-Arg(NO$_2$)CH$_2$Cl. The product was treated with HF (7 ml) and anisole (0.5 ml) at 0° C. for 20 min. After the HF was removed, the residue was diluted with cold H$_2$O and washed with diethyl ether two times (5 ml each). The organic volatiles were removed under reduced pressure before lyophilizing the crude H-L-Asp-L-Thr-L-Arg-CMK.2HF to a powder. A crude purification of the material was accomplished on a Sephadex SP-C25 (H+form) column using 0–1.0N HCl stepwise gradient which yielded H-L-Asp-L-Thr-L-Arg-CMK.2HCl. The product was further purified on a Supelco LCNH$_2$ column eluted with a 10–50% (v/v) hexane/isopropanol (10% methanol) gradient, and dried in vacuo. The product was characterized by 360 MHz $^1$H NMR. The product was dissolved in water, methanol or suitable aqueous solutions for analysis or other uses.

(b) Peptide Synthesis Using Solid Phase Technique.

Preparation of H-Arg-(NO$_2$)CH$_2$Cl.HCl. See Example 8(*b*).

Preparation of H-Asp-Thr-Arg-CMK. The preformed peptide Boc-Asp-O-Bzl-Thr-OH (1 mmol) was allowed to react with N-methylmorpholine (1 mmol) in 5 ml of THF for 10 min at −20° C. H-Arg(NO$_2$)CH$_2$Cl.HCl (1 mmol) dissolved in 5 ml of cold N,N-dimethylformamide was added to the mixed anhydride preparation. After 15 min was added cold THF (20 ml) containing triethylamine (1 mmol). After stirring for 1 hr at −20° C. and 2 hr at room temperature, the reaction mixture was filtered, the filtrate was suspended in ethyl acetate and the ethyl acetate layer was washed with water before being evaporated to dryness. The crude product was deprotected by HF cleavage [anisole:crude product:HF (1:1:10)] for 60 min at 0° C. and an aqueous suspension of the crude product was washed 3 times with ether followed by three washes with chloroform. The combined organic layers were washed sequentially with 0.1N HCl, H$_2$O, 1M K$_2$CO$_3$ and saturated NaCl, dried over MgSO$_4$ and the solvent was removed in vacuo. The product was purified on a Vydac C-18 column eluted with a 10–40% (v/v) acetonitrile in H$_2$O containing 0.1% (v/v) TFA gradient, and dried under vacuo. The product was dissolved in water or suitable aqueous solution for analysis or other uses.

EXAMPLE 10 Synthesis of H-L-His-L-Thr-L-Arg-CMK (a) Peptide Synthesis Using Solution Phase Technique.

Preparation of H-L-Arg(NO$_2$)CH$_2$Cl.HCl. Boc-L-Arg(NO$_2$)OH was first converted to Boc-L-Arg(NO$_2$)CNH$_2$ and then to H-L-Arg(NO$_2$)CH$_2$Cl.HCl, using the procedure exactly as described in Example 8.

Preparation of N-α-cbz-N-im-tosyl-L-His-L-(O-t-butyl)-ThrOH. N-α-cbz-N-im-tosyl-L-HisOH (0.01 mol) was coupled to L-(O-t-butyl)-ThrOMe (0.01 mol) to form N-α-cbz-N-im-tosyl-L-His-L-(O-t-butyl)-ThrOMe which was deesterified to yield N-α-cbz-N-im-tosyl-L-His-L-(O-t-butyl)-ThrOH, using the procedure outlined in Example 8 for the preparation of Cbz-L-Asn-L-(O-t-butyl)-ThrOH.

Preparation of H-L-His-L-Thr-L-Arg-CMK. The preformed protected dipeptide, N-α-cbz-N-im-tosyl-L-

His-L-(O-t-butyl)-ThrOH, (2.0 mmol) was allowed to react with isobutyl chloroformate (0.29 ml, 2.1 mmol), in the presence of N-methylmorpholine (0.24 ml, 2.1 mmol) at 0° C. for 20 min. A solution of H-L-Arg(NO$_2$)CH$_2$Cl.HCl (0.60 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with H$_2$O and brine (25 ml each), extracted two times with ethyl acetate (25 ml each). The combined organic layers were washed with 10% citric acid, saturated NaHCO$_3$ and brine (15 ml each), dried over MgSO$_4$, and the solvent was removed in vacuo to give N-α-cbz-N-im-tosyl-L-His-L-(O-t-butyl)-Thr-L-Arg(NO$_2$)CH$_2$Cl. The product was treated with HF (7 ml) and anisole (0.5 ml) at 0° C. for 20 min. After the HF was removed, the residue was diluted with cold H$_2$O and washed with diethyl ether twice (5 ml each). The organic volatiles were removed under reduced pressure before lyophilizing the crude H-L-His-L-Thr-L-Arg-CMK.2HF to a powder. A crude purification of the material was accomplished on a Sephadex SP-C25 (H+form) column using 0–1.0N HCl stepwise gradient which yielded H-L-His-L-Thr-L-Arg-CMK.2HCl. The product was further purified on a Supelco LCNH$_2$ column eluted with a 10–50% v/v hexane/isopropanol (10% methanol) gradient, and dried in vacuo. The product was characterized by 360 MHz $^1$H NMR. The product was dissolved in water, methanol, or suitable aqueous solutions for analysis or other uses.

(b) Peptide Synthesis Using Solid Phase Technique.

Preparation of H-L-Arg(NO$_2$)CH$_2$Cl.HCl. See Example 8(b).

Preparation of H-His-Thr-Arg-CMK. The preformed peptide N-α-Boc-N-im-Cbz-His-O-Bzl-ThrOH (1 mmol) was allowed to react with N-methylmorpholine (1 mmol) in 5 ml of THF for 10 min at −20° C. H-Arg(NO$_2$)CH$_2$Cl.HCl (1 mmol) dissolved in 5 ml of cold N,N-dimethylformamide was added to the mixed anhydride preparation. After 15 min was added cold THF (20 ml) containing triethylamine (1 mmol). After stirring for 1 hr at −20° C. and 2 hr at room temperature, the reaction mixture was filtered, the filtrate was suspended in ethyl acetate and the ethyl acetate layer was washed with water before being evaporated to dryness. The crude product was deprotected by HF cleavage [anisole:crude product:HF (1:1:10)] for 60 min at 0° C. and an aqueous suspension of the crude product was washed 3 times with ether followed by three washes with chloroform. The combined organic layers were washed sequentially with 0.1N HCl, H$_2$O, 1M K$_2$CO$_3$ and saturated NaCl, dried over MgSO$_4$ and the solvent was removed in vacuo. The product was purified on a Vydac C-18 column eluted with a 10–40% (v/v) acetonitrile in H$_2$O containing 0.1% (v/v) TFA gradient, and dried under vacuo. The product was dissolved in water or suitable aqueous solution for analysis or other uses.

EXAMPLE 11

Synthesis of H-L-Leu-L-Thr-L-Arg-CMK (a) Peptide Synthesis Using Solution Phase Technique.

Preparation of H-L-Arg(NO$_2$)CH$_2$Cl.HCl. Boc-L-Arg-(NO$_2$)OH was first converted to Boc-L-Arg-(NO$_2$)CNH$_2$ and then transformed to H-L-Arg-(NO$_2$)CH$_2$Cl.HCl, using the procedure exactly as described in Example 8.

Preparation of Cbz-L-Leu-L-(O-t-butyl)-ThrOH. Cbz-L-LeuOH (0.01 mol) was coupled to L-(O-t-butyl)-ThrOMe (0.01 mol) to form Cbz-L-Leu-L-(O-t-butyl)-ThrOMe which was deesterified to yield Cbz-L-Leu-L-(O-t-butyl)-ThrOH, using the procedure outlined in Example 8 for the preparation of Cbz-L-Asn-L-(O-t-butyl)-ThrOH.

Preparation of H-L-Leu-L-Thr-L-Arg-CMK. The preformed protected dipeptide, Cbz-L-Leu-L-(O-t-butyl)-ThrOH, (2.0 mmol) was allowed to react with isobutyl chloroformate (0.29 ml, 2.1 mmol), in the presence of N-methylmorpholine (0.24 ml, 2.1 mmol) at 0° C. for 20 min. A solution of H-L-Arg(NO$_2$)CH$_2$Cl.HCl (0.6 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with H$_2$O and brine (25 ml each), extracted two times with ethyl acetate (25 ml each). The combined organic layers were washed with 10% citric acid, saturated NaHCO$_3$ and brine (15 ml each), dried over MgSO$_4$, and the solvent was removed in vacuo to give Cbz-L-Leu-L-(O-t-butyl)-Thr-L-Arg(NO$_2$)CH$_2$Cl. The product was treated with HF (7 ml) and anisole (0.5 ml) at 0° C. for 20 min. After the HF was removed, the residue was diluted with cold H$_2$O and washed with diethyl ether two times (5 ml each). The organic volatiles were removed under reduced pressure before lyophilizing the crude H-L-Leu-L-thr-L-Arg-CMK.2HF to a powder. A crude purification of the material was accomplished on a Sephadex SP-C25 (H+form) column using 0–1.0N HCl stepwise gradient which yielded H-L-Leu-L-Thr-L-Arg-CMK.2HCl. The product was further purified on a Supelco LCNH$_2$ column eluted with a 10–50% (v/v) hexane/isopropanol (10% methanol) gradient, and dried in vacuo. The product was characterized by 360 MHz $^1$H NMR. The product was dissolved in water, methanol, or suitable aqueous solutions for analysis or other uses.

(b) Peptide Synthesis Using Solid Phase Technique.

Preparation of H-Arg(NO$_2$)CH$_2$Cl.HCl. See Example 8(b).

Preparation of H-Leu-Thr-Arg-CMK. The preformed peptide Boc-Leu-O-Bzl-Thr-OH (1 mmol), was allowed to react with N-methylmorpholine (1 mmol) in 5 ml of THF for 10 min at −20° C. H-Arg(NO$_2$)CH$_2$Cl.HCl (1 mmol) dissolved in 5 ml of cold N,N-dimethylformamide was added to the mixed anhydride preparation. After 15 min was added cold THF (20 ml) containing triethylamine (1 mmol). After stirring for 1 hr at −20° C. and 2 hr at room temperature, the reaction mixture was filtered, the filtrate was suspended in ethyl acetate and the ethyl acetate layer was washed with water before being evaporated to dryness. The crude product was deprotected by HF cleavage [anisole:crude product:HF (1:1:10)] for 60 min at 0° C. and an aqueous suspension of the crude product was washed 3 times with ether followed by three washes with chloroform. The combined organic layers were washed sequentially with 0.1N HCl, H$_2$O, 1M K$_2$CO$_3$ and saturated NaCl, dried over MgSO$_4$ and the solvent was removed in vacuo. The product was purified on a Vydac C-18 column eluted with a 10–40% (v/v) acetonitrile in H$_2$O containing 0.1% (v/v) TFA gradient, and dried under vacuo. The product was dissolved in water or suitable aqueous solution for analysis or other uses.

EXAMPLE 12

Synthesis of H-L-Gln-L-Thr-L-Arg-CMK (a) Peptide Synthesis Using Solution Phase Technique.

Preparation of H-L-Arg($NO_2$)$CH_2$Cl.HCl. Boc-L-Arg-($NO_2$)OH is first converted to Boc-L-Arg($NO_2$)$CNH_2$ and then transformed to H-L-Arg($NO_2$)$CH_2$Cl.HCl, using the procedure exactly as described in Example 8.

Preparation of Cbz-L-Gln-L-(O-t-butyl)-ThrOH. Cbz-L-GlnOH (0.01 mol) is coupled to L-(O-t-butyl)-ThrOMe (0.01 mol) to form Cbz-L-Gln-L-(O-t-butyl)-ThrOMe which is then deesterified to yield Cbz-L-Gln-L-(O-t-butyl)-ThrOH, using the procedure outlined in Example 8 for the preparation of Cbz-L-Asn-L-(O-t-butyl)-ThrOH.

Preparation of H-L-Gln-L-Thr-L-Arg-CMK. The preformed protected dipeptide, Cbz-L-Gln-L-(O-t-butyl)-ThrOH, (2.0 mmol) is allowed to react with isobutyl chloroformate (0.29 ml, 2.1 mmol), in the presence of N-methylmorpholine (0.24 ml, 2.1 mmol) at 0° C. for 20 min. A solution of H-L-Arg($NO_2$)$CH_2$Cl.HCl (0.60 g, 2.0 mmol) in dimethylformamide (4 ml) is added dropwise. After stirring for 20 min at 0° C., N-methylmorpholine (0.22 ml, 2.0 mmol) in THF is added. The resulting solution is stirred at 0° C. for an additional 40 min, then at RT for 1 hr. The reaction mixture is diluted with $H_2O$ and brine (25 ml each), extracted two times with ethyl acetate (25 ml each). The combined organic layers are washed with 10% citric acid, saturated NaH$CO_3$ and brine (15 ml each), dried over $MgSO_4$, and the solvent is removed in vacuo to give Cbz-L-Gln-L-(O-t-butyl)-Thr-L-Arg($NO_2$)$CH_2$Cl. The product is treated with HF (7 ml) and anisole (0.5 ml) at 0° C. for 20 min. After the HF is removed, the residue is diluted with cold $H_2O$ and washed with diethyl ether two times (5 ml each). The organic volatiles are removed under reduced pressure before lyophilizing the crude H-L-Gln-L-Thr-L-Arg-CMK.2HF to a powder. A crude purification of the material is accomplished on a Sephadex SP-C25 (H+form) column using 0–1.0N HCl stepwise gradient which yields H-L-Gln-L-Thr-L-Arg-CMK.2HCl. The product is further purified on a Supelco LC$NH_2$ column eluted with a 10–50% (v/v) hexane/isopropanol (10% methanol) gradient, and dried in vacuo. The product is characterized by 360 MHz $^1$H NMR. The product is dissolved in water, methanol, or suitable aqueous solutions for analysis or other uses.

(b) Peptide Synthesis Using Solid Phase Technique.

Preparation of H-L-Arg($NO_2$)$CH_2$Cl.HCl. See Example 8(b).

Preparation of H-Gln-Thr-Arg-CMK. The preformed peptide Boc-Gln-O-Bzl-Thr-OH (1 mmol) is allowed to react with N-methylmorpholine (1 mmol) in 5 ml of THF for 10 min at −20° C. H-Arg($NO_2$)$CH_2$Cl.HCl (1 mmol) dissolved in 5 ml of cold N,N-dimethylformamide is added to the mixed anhydride preparation. After 15 min is added cold THF (20 ml) containing triethylamine (1 mmol). After stirring for 1 hr at −20° C. and 2 hr at room temperature, the reaction mixture is filtered, the filtrate suspended in ethyl acetate and the ethyl acetate layer is washed with water before being evaporated to dryness. The crude product is deprotected by HF cleavage [anisole:crude product:HF (1:1:10)] for 60 min at 0° C. and an aqueous suspension of the crude product is washed 3 times with ether followed by three washes with chloroform. The combined organic layers are washed sequentially with 0.1N HCl, $H_2O$, 1M $K_2CO_3$ and saturated NaCl, dried over $MgSO_4$ and the solvent is removed in vacuo. The product is purified on a Vydac C-18 column eluted with a 10–40% (v/v) acetonitrile in $H_2O$ containing 0.1% (v/v) TFA gradient, and dried under vacuo. The product is dissolved in water or suitable aqueous solution for analysis or other uses.

EXAMPLE 13

Synthesis of H-L-Thr-L-Thr-L-Arg-CMK (a) Peptide Synthesis Using Solution Phase Technique.

Preparation of H-L-Arg($NO_2$)$CH_2$CL.HCl. Boc-L-Arg($NO_2$)OH is first converted to Boc-L-Arg($NO_2$)$CNH_2$ and then transformed to H-L-Arg($NO_2$)$CH_2$Cl.HCl, using the procedure exactly as described in Example 8.

Preparation of Cbz-L-(O-t-butyl)-Thr-L-(O-t-butyl)-ThrOH. Cbz-L-(O-t-butyl)-ThrOH (0.01 mol) is coupled to L-(O-t-butyl)-ThrOMe (0.01 mol) to form Cbz-L-(O-t-butyl)-Thr-L-(O-t-butyl)ThrOMe which is then deesterified to yield Cbz-L-(O-t-butyl)-Thr-L-(O-t-butyl)-ThrOH, using the procedure outlined in Example 8 for the preparation of Cbz-L-Asn-L-(O-t-butyl)-ThrOH.

Preparation of H-L-Thr-L-Thr-L-Arg-CMK. The preformed protected dipeptide, Cbz-L-(O-t-butyl)-Thr-L-(O-t-butyl)-ThrOH, (2.0 mmol) is allowed to react with isobutyl chloroformate (0.29 ml, 2.1 mmol), in the presence of N-methylmorpholine (0.24 ml, 2.1 mmol) at 0° C. for 20 min. A solution of H-L-Arg($NO_2$)$CH_2$Cl.HCl (0.60 g, 2.0 mmol) in dimethylformamide (4 ml) is added dropwise. After stirring for 20 min at 0° C., N-methylmorpholine (0.22 ml, 2.0 mmol) in THF is added. The resulting solution is stirred at 0° C. for an additional 40 min, then at RT for 1 hr. The reaction mixture is diluted with $H_2O$ and brine (25 ml each), extracted two times with ethyl acetate (25 ml each). The combined organic layers are washed with 10% citric acid, saturated NaH$CO_3$ and brine (15 ml each), dried over $MgSO_4$, and the solvent is removed in vacuo to give Cbz-L-(O-t-butyl)-Thr-L-(O-t-butyl)-Thr-L-Arg($NO_2$)$CH_2$Cl. The product is treated with HF (7 ml) and anisole (0.5 ml) at 0° C. for 20 min. After the HF is removed, the residue is diluted with cold $H_2O$ and washed with diethyl ether two times (5 ml each). The organic volatiles are removed under reduced pressure before lyophilizing the crude H-L-Thr-L-Thr-L-Arg-CMK.2HF to a powder. A crude purification of the material is accomplished on a Sephadex SP-C25 (H+form) column using 0–1.0N HCl stepwise gradient which yields H-L-Thr-L-Thr-L-Arg-CMK.2HCl. The product is further purified on a Supelco LC$NH_2$ column eluted with a 10–50% (v/v) hexane/isopropanol (10% methanol) gradient, and dried in vacuo. The product is characterized by 360 MHz $^1$H NMR. The product is dissolved in water, methanol, or suitable aqueous solutions for analysis or other uses.

(b) Peptide Synthesis Using Solid Phase Technique.

Preparation of H-L-Arg($NO_2$)$CH_2$Cl.HCl. See Example 8(b).

Preparation of H-Thr-Thr-Arg-CMK. The preformed peptide Boc-O-Bzl-Thr-O-Bzl-Thr-OH (1 mmol) is allowed to react with N-methylmorpholine (1 mmol) in 5 ml of THF for 10 min at −20° C. H-Arg($NO_2$)$CH_2$Cl.HCl (1 mmol) dissolved in 5 ml of cold N,N-dimethylformamide is added to the mixed anhydride preparation. After 15 min is added cold THF (20 ml) containing triethylamine (1 mmol). After stirring for 1 hr at −20° C. and 2 hr at room temperature, the reaction mixture is filtered, the filtrate is suspended in ethyl acetate and the ethyl acetate layer is washed with water before being evaporated to dryness. The crude product is deprotected by HF cleavage [anisole:-crude product:HF (1:1:10)] for 60 min at 0° C. and an aqueous suspension of the crude product is washed 3 times with ether followed by three washes with chloroform. The combined organic layers are washed sequentially with 0.1N HCl, $H_2O$, 1M $K_2CO_3$ and saturated NaCl, dried over $MgSO_4$ and the solvent is removed in vacuo. The product is purified on a Vydac C-18 column eluted with a 10–40% (v/v) acetonitrile in $H_2O$ containing 0.1% (v/v) TFA gradient, and dried under vacuo. The product is dissolved in water or suitable aqueous solution for analysis or other uses.

EXAMPLE 14

Synthesis of H-L-Thr-L-Arg-CMK

Preparation of H-Arg($NO_2$)$CH_2$Cl.HCl. The procedure exactly as described in Example 8 can be used to make the desired chloromethyl ketone.

Preparation of H-L-Thr-L-Arg-CMK. Cbz-L-(O-t-butyl)-ThrOH (2.0 mmol) is allowed to react with isobutyl chloroformate (0.29 ml, 2.1 mmol), in the presence of N-methylmorpholine (0.24 ml, 2.1 mmol) at 0° C. for 20 min. A solution of H-L-Arg($NO_2$)$CH_2$Cl.HCl (0.60 g, 2.0 mmol) in dimethylformamide (4 ml) is added dropwise. After stirring for 20 min at 0° C., N-methylmorpholine (0.22 ml, 2.0 mmol) in THF is added. The resulting solution is stirred at 0° C. for an additional 40 min, then at RT for 1 hr. The reaction mixture is diluted with $H_2O$ and brine (25 ml each), extracted twice with ethyl acetate (25 ml each). The combined organic layers are washed with 10% citric acid, saturated $NaHCO_3$ and brine (15 ml each), dried over $MgSO_4$, and the solvent is removed in vacuo to give Cbz-L-(O-t-butyl)-Thr-L-Arg($NO_2$)$CH_2$Cl. The product is treated with HF (7 ml) and anisole (0.5 ml) at 0° C. for 20 min. After the HF is removed, the residue is diluted with cold $H_2O$ and washed with diethylether two times (5 ml each). The organic volatiles are removed under reduced pressure before lyophilizing the crude H-L-Thr-L-Arg-CMK.2HF to a powder. A crude purification of the material is accomplished on a Sephadex SP-C25 (H+form) column using 0–1.0N HCl stepwise gradient which yields H-L-Thr-L-Arg-CMK.2HCl. The product is further purified on a Supelco LCNH2 column eluted with a 10–50% (v/v) hexane/isopropanol (10% methanol) gradient, and dried in vacuo. The product is characterized by 360 MHz $^1$H NMR. The product is dissolved in water, methanol, or suitable aqueous solutions for analysis or other uses.

EXAMPLE 15

Synthesis of H-D-Leu-L-Thr-L-Arg-CMK

The synthesis of H-D-Leu-L-Thr-L-Arg-CMK was performed as described in Example 11, except that Cbz-D-LeuOH was substituted for the L-isomer.

EXAMPLE 16

Synthesis of H-D-Phe-L-Thr-L-Arg-CMK

Preparation of H-Arg($NO_2$)$CH_2$Cl.HCl. Boc-L-Arg($NO_2$)OH was first converted to Boc-L-Arg($NO_2$)$CNH_2$ and then transformed to H-L-Arg($NO_2$)$CH_2$Cl.HCl, using the procedure exactly as described in Example 8.

Preparation of Cbz-D-Phe-L-(O-t-butyl)-ThrOH. Cbz-D-PheOH (0.01 mol) was coupled to L-(O-t-butyl)-ThrOMe (0.01 mol) to form Cbz-D-Phe-L-(O-t-butyl)-ThrOMe which was then deesterified to yield Cbz-D-Phe-L-(O-t-butyl)-ThrOH, using the procedure outlined in Example 8 for the preparation of Cbz-L-Asn-L-(O-t-butyl)-ThrOH.

Preparation of H-D-Phe-L-Thr-L-Arg-CMK. The preformed protected dipeptide, Cbz-D-Phe-L-(O-t-butyl)-ThrOH, (2.0 mmol) was allowed to react with isobutyl chloroformate (0.29 ml, 2.1 mmol), in the presence of N-methylmorpholine (0.24 ml, 2.1 mmol) at 0° C. for 20 min. A solution of H-L-Arg($NO_2$)$CH_2$Cl.HCl (0.60 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with $H_2O$ and brine (25 ml each), extracted twice with ethyl acetate (25 ml each). The combined organic layers were washed with 10% citric acid, saturated $NaHCO_3$ and brine (15 ml each), dried over $MgSO_4$, and the solvent was removed in vacuo to give Cbz-D-Phe-L-(O-t-butyl)-Thr-L-Arg($NO_2$)$CH_2$Cl. The product was treated with HF (7 ml) and anisole (0.5 ml) at 0° C. for 20 min. After the HF was removed, the residue was diluted with cold $H_2O$ and washed with diethyl ether two times (5 ml each). The organic volatiles were removed under reduced pressure before lyophilizing the crude H-D-Phe-L-Thr-L-Arg-CMK.2HF to a powder. A crude purification of the material was accomplished on a Sephadex SP-C25 (H+form) column using 0–1.0N HCl stepwise gradient which yielded H-D-Phe-L-Thr-L-Arg-CMK.2HCl. The product was further purified on a Supelco LCNH2 column eluted with a 10–50% (v/v) hexane/isopropanol (10% methanol) gradient, and dried in vacuo. The product was characterized by 360 MHz $^1$H NMR. The product was dissolved in water, methanol, or suitable aqueous solutions for analysis or other uses.

EXAMPLE 17

Synthesis of Ac-L-Leu-L-Thr-L-Arg-CMK

H-L-Leu-L-Thr-L-Arg-CMK was synthesized as described in Example 4. To 36 μmol (16.4 mg brought to 1 ml with $H_2O$) of the H-L-Leu-L-Thr-L-Arg-CMK was added 1 equivalent of 1N NaOH followed by a 30% excess of acetic anhydride and an additional equivalent of 1N NaOH. The resulting solution was incubated for 2 hr, lyophilized and purified on a Sephadex SP-C25 column. The product was characterized by 360 MHz $^1$H NMR.

EXAMPLE 18

Synthesis of Tosyl-L-Leu-L-Thr-L-Arg-CMK

H-L-Leu-L-Thr-L-Arg-CMK was synthesized as described in Example 4. To 43 μmol (19.8 mg brought to 1 ml with $H_2O$) of the H-L-Leu-L-Thr-L-Arg-CMK were added sequentially 1 equivalent of 1N NaOH, 1.4 equivalents of tosyl (toluene sulfonyl) chloride, 2 ml of acetonitrile and 1 additional equivalent of 1N NaOH. The solution was stirred and then allowed to stand for 6 hr, after which acetonitrile was removed by rotatory evaporation. The product was purified chromatographically and subsequently characterized by 360 MHz $^1$H NMR.

EXAMPLE 19

Synthesis of Dansyl-L-Leu-L-Thr-L-Arg-CMK

H-L-Leu-L-Thr-L-Arg-CMK was synthesized as described in Example 4. To 37 μmol (17 mg to which 0.3 ml H$_2$O is added) of H-L-Leu-L-Thr-L-Arg-CMK were added sequentially 1 equivalent of 1N NaOH, 1.4 equivalents of dansyl (5-dimethylaminonaphthalenesulfonyl) chloride, 0.5 ml acetonitrile and 1 additional equivalent of 1N NaOH. After stirring, the solution was allowed to stand for 6 hr at RT, followed by incubation at −20° C. for 16 hr. Acetonitrile was removed by rotatory evaporation. The product was purified chromatographically before being characterized by 360 MHz $^1$H NMR.

EXAMPLE 20

Synthesis of H-L-Leu-L-Ser-L-Arg-CMK

Preparation of H-Arg(NO$_2$)CH$_2$Cl.HCl. Boc-L-Arg(NO$_2$)OH was first converted to Boc-L-Arg(NO$_2$)CNH$_2$ and then transformed to H-L-Arg(NO$_2$)CH$_2$Cl.HCl, using the procedure exactly as described in Example 8.

Preparation of Cbz-L-Leu-L-(O-t-butyl)-SerOH. CBz-L-LeuOH (0.01 mol) was coupled to L-(O-t-butyl)-SerOMe (0.01 mol) to form Cbz-L-Leu-L-(O-t-butyl)-SerOMe which was then deesterified to yield Cbz-L-Leu-L-(O-t-butyl)-SerOH, using the procedure outlined in Example 8 for the preparation of Cbz-L-Asn-L-(O-t-butyl)-ThrOH.

Preparation of H-L-Leu-L-Ser-L-Arg-CMK. The preformed protected dipeptide, Cbz-L-Leu-L-(O-t-butyl)-SerOH, (2.0 mmol) was allowed to react with isobutyl chloroformate (0.29 ml, 2.1 mmol), in the presence of N-methylmorpholine (0.24 ml, 2.1 mmol) at 0° C. for 20 min. A solution of H-L-Arg(NO$_2$)CH$_2$Cl.HCl (0.60 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with H$_2$O and brine (25 ml each), extracted twice with ethyl acetate (25 ml each). The combined organic layers were washed with 10% citric acid, saturated NaHCO$_3$ and brine (15 ml each), dried over MgSO$_4$, and the solvent was removed in vacuo to give Cbz-L-Leu-L-(O-t-butyl)-Ser-L-Arg(NO$_2$)CH$_2$Cl. The product was treated with HF (7 ml) and anisole (0.5 ml) at 0° C. for 20 min. After the HF was removed, the residue was diluted with cold H$_2$O and washed with diethyl ether two times (5 ml each). The organic volatiles were removed under reduced pressure before lyophilizing the crude H-L-Leu-L-Ser-L-Arg-CMK.2HF to a powder. A crude purification of the material was accomplished on a Sephadex SP-C25 (H+form) column using 0–1.0N HCl stepwise gradient which yielded H-L-Leu-L-Ser-L-Arg-CMK.2HCl. The product was further purified on a Supelco LCNH$_2$ column eluted with a 10–50% (v/v) hexane/isopropanol (10% methanol) gradient, and dried in vacuo. The product was characterized by 360 MHz $^1$H NMR. The product was dissolved in water, methanol, or suitable aqueous solutions for analysis or other uses.

EXAMPLE 21

Synthesis of H-L-Leu-L-Pro-L-Arg-CMK

Preparation of H-Arg(NO$_2$)CH$_2$Cl HCl. Boc-L-Arg(NO$_2$)OH was first converted to Boc-L-Arg(NO$_2$)CNH$_2$ and then transformed to H-L-Arg(NO$_2$)CH$_2$Cl.HCl, using the procedure exactly as described in Example 8.

Preparation of Cbz-L-Leu-L-ProOH. Cbz-L-LeuOH (0.01 mol) was coupled to L-ProOMe (0.01 mol) to form Cbz-L-Leu-L-ProOMe which was then deesterified to yield Cbz-L-Leu-L-ProOH, using the procedure outlined in Example 8 for the preparation of Cbz-L-Asn-L-(O-t-butyl)-ThrOH.

Preparation of H-L-Leu-L-Pro-L-Arg-CMK. The preformed protected dipeptide, Cbz-L-Leu-L-ProOH, (2.0 mmol) was allowed to react with isobutyl chloroformate (0.29 ml, 2.1 mmol), in the presence of N-methylmorpholine (0.24 ml, 2.1 mmol) at 0° C. for 20 min. A solution of H-L-Arg(NO$_2$)CH$_2$Cl.HCl (0.60 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with H$_2$O and brine (25 ml each), extracted twice with ethyl acetate (25 ml each). The combined organic layers were washed with 10% citric acid, saturated NaHCO$_3$ and brine (15 ml each), dried over MgSO$_4$, and the solvent was removed in vacuo to give Cbz-L-Leu-L-Pro-L-Arg(NO$_2$)CH$_2$Cl. The product was treated with HF (7 ml) and anisole (0.5 ml) at 0° C. for 20 min. After the HF was removed, the residue was diluted with cold H$_2$O and washed with diethyl ether two times (5 ml each). The organic volatiles were removed under reduced pressure before lyophilizing the crude H-L-Leu-L-Pro-L-Arg-CMK.2HF to a powder. A crude purification of the material was accomplished on a Sephadex SP-C25 (H+form) column using 0–1.0N HCl stepwise gradient which yielded H-L-Leu-L-pro-L-Arg-CMK.2HCl. The product was further purified on a Supelco LCNH$_2$ column eluted with a 10–50% (v/v) hexane/isopropanol (10% methanol) gradient, and dried in vacuo. The product was characterized by 360 MHz $^1$H NMR. The product was dissolved in water, methanol, or suitable aqueous solutions for analysis or other uses.

EXAMPLE 22

Synthesis of H-L-Asn-L-Ser-L-Arg-CMK

Preparation of H-Arg(NO$_2$)CH$_2$Cl.HCl. Boc-L-Arg(NO$_2$)OH was first converted to Boc-L-Arg(NO$_2$)CNH$_2$ and then transformed to H-L-Arg(NO$_2$)CH$_2$Cl.HCl, using the procedure exactly as described in Example 8.

Preparation of Cbz-L-Asn-L-(O-t-butyl)-SerOH. Cbz-L-AsnOH (0.01 mol) was coupled to L-(O-t-butyl)-SerOMe (0.01 mol) to form Cbz-L-Asn-L-(O-t-butyl)-SerOMe which was then deesterified to yield Cbz-L-Asn-L-(O-t-butyl)-SerOH, using the procedure outlined in Example 8 for the preparation of Cbz-L-Asn-L-(O-t-butyl)-ThrOH.

Preparation of H-L-Asn-L-Ser-L-Arg-CMK. The preformed protected dipeptide, Cbz-L-Asn-L-(O-t-butyl)-SerOH, (2.0 mmol) was allowed to react with isobutyl chloroformate (0.29 ml, 2.1 mmol), in the presence of N-methylmorpholine (0.24 ml, 2.1 mmol) at 0° C. for 20 min. A solution of H-L-Arg(NO₂)CH₂Cl.HCl (0.60 g, 2.0 mmol) in dimethylformamide (4 ml) was added dropwise. After stirring for 20 min at 0° C., N-methylmorpholine (0.22 ml, 2.0 mmol) in THF was added. The resulting solution was stirred at 0° C. for an additional 40 min, then at RT for 1 hr. The reaction mixture was diluted with H₂O and brine (25 ml each), extracted twice with ethyl acetate (25 ml each). The combined organic layers were washed with 10% citric acid, saturated NaHCO₃ and brine (15 ml each), dried over MgSO₄, and the solvent was removed in vacuo to give Cbz-L-Asn-L-(O-t-butyl)-Ser-L-Arg(NO₂)CH₂Cl. The product was treated with HF (7 ml) and anisole (0.5 ml) at 0° C. for 20 min. After the HF was removed, the residue was diluted with cold H₂O and washed with diethyl ether two times (5 ml each). The organic volatiles were removed under reduced pressure before lyophilizing the crude H-L-Asn-L-Ser-L-Arg-CMK.2HF to a powder. A crude purification of the material was accomplished on a Sephadex SP-C25 (H+form) column using 0-1.0N HCl stepwise gradient which yielded H-L-Asn-L-Ser-L-Arg-CMK.2HCl. The product was further purified on a Supelco LCNH₂ column eluted with a 10-50% (v/v) hexane/isopropanol (10% methanol) gradient, and dried in vacuo. The product was characterized by 360 MHz ¹H NMR. The product was dissolved in water, methanol, or suitable aqueous solutions for analysis or other uses.

EXAMPLE 23

Clotting inhibition

Normal human plasma was diluted 1:3 by volume with 0.02 M Na Citrate, 0.14M NaCl pH 7.4 in a glass tube. Diluted plasma (100μl) was then mixed with 100μl of J82 cells at 1×10⁶ cells/ml and 100 μl of inhibitor. Plasma clotting times were obtained by visual observation of initial turbidity following addition of 100 μl of 20 mM calcium chloride. Results are shown in Table 4. Human plasma clotting times were also expressed as calculated milli-units of TF activity (assuming no inhibitor present). The data show that LTR-CMK is an effective inhibitor of the proteolytic activation of clotting by [TF:VII/VIIa] complex.

TABLE 4

Specific Inhibition of Clotting of Normal Human Plasma by LTR—CMK*

| LTR—CMK Final Conc (μM) | Human Plasma Clotting Time | [TF:VII/VIIa] Activity (mU)** | Inhibition |
|---|---|---|---|
| 300 | 120 s | 11.0 | 75.0% |
| 30 | 102 s | 25.4 | 41.0% |
| 3 | 93 s | 40.9 | 5.3% |
| 0 | 92 s | 43.2 | 0 |

*LTR—CMK represents H—L—Leu—L—Thr—L—Arg—chloromethyl ketone.
**A calculated activity to indicate the level of [TF:VII/VIIa] activity present in the sample, assuming absence of inhibitor. The conversion factor used was: 1000 milli units (mU) = 50 s.

We claim:
1. A compound having the formula

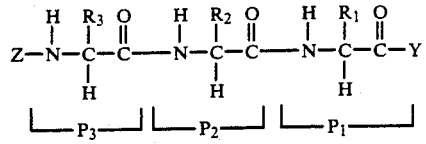

wherein R₁ is an arginine side chain —(CH₂)₃—NH—CNHNH₂, R₂ is a threonine side chain —CHOH—CH₃, or serine side chain —CH₂OH or proline side chain —(CH₂)₃— such that P₂ is proline except when P₃ is D-phenylalanine, R₃ is a side chain of asparagine —CH₂—CONH₂, aspartic acid —CH₂—COO⁻, histidine

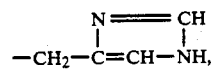

leucine —CH₂—CH—[CH₃]₂, glutamine —(CH₂)₂—CONH₂, threonine —CHOH—CH₃ or phenylalanine

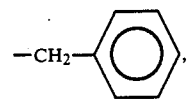

and oriented so that P₃ is either in the L or D form; Y is hydroxy or a straight or branched alkoxy group with one to four carbon atoms, benzyloxy, NA₁A₂ where each of A₁ and A₂ is H or alkyl of one to four carbon atoms, a chloromethyl or a fluoromethyl; Z is H, straight or branched alkyl, CH or CHO ring group, or CHO having one to six carbon atoms either unsubstituted or substituted by formyl or tert-butyloxycarbonyl, or by dansyl or tosyl.

2. The compound of claim 1 wherein

is a chloromethyl ketone or fluoromethyl ketone is H.

3. The compound of claim 1 wherein

is chloromethyl ketone and Z is H.

4. The compound of claim 1 wherein Y is hydroxy and Z is H.

5. The compound of claim 1 wherein Y is hydroxy, Z is H and R₃ is —CH₂—CH—(CH₃)₂.

6. The compound of claim 1 wherein Y is hydroxy, Z is H and R₃ is

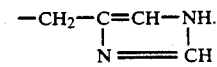

7. The compound of claim 1 wherein Y is hydroxy, Z is H and R₃ is —CHOH—CH₃.

8. The compound of claim 1 wherein Y is hydroxy, Z is H and R₃ is —CH₂—CONH₂.

9. The compound of claim 1 wherein Y is hydroxy, Z is H and R₃ is —CH₂—COOH.

10. The compound of claim 1 wherein Y is hydroxy, Z is H and R₃ is —(CH₂)₂—CONH₂.

11. The compound of claim 1 wherein

is chloromethyl ketone, Z is H, R₂ is selected from the group consisting of —CHOH—CH₃, —CH₂OH and —(CH₂)₃— such that P₂ is proline except when P₃ is D-phenylalanine, and R₃ is selected from the group consisting of CH₂—CH—(CH₃)₂,

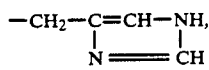

—CHOH—CH₃, —CH₂—CONH₂, —CH₂—COOH, —(CH₂)₂—CONH₂ and

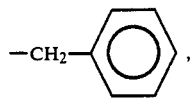

and oriented so that P₃ is either in the L or D form.

12. The compound of claim 1 wherein

is chloromethyl ketone, Z is H, R₂ is the threonine side chain —CHOH—CH₃, and R₃ is the leucine side chain —CH₂—CH-(CH₃)₂.

13. The compound of claim 12 wherein the amino acid at the P₃ site is the D-isomer.

14. The compound of claim 1 wherein

is chloromethyl ketone, Z is selected from the group consisting of acetyl, tosyl and dansyl groups, R₂ is the threonine side chain —CHOH—CH₃, and R₃ is the leucine side chain —CH₂CH(CH₃)₂.

15. The compound of claim 1 wherein

is chloromethyl ketone, Z is H, R₂ is the serine side chain —CH₂OH and R₃ is the leucine side chain —CH₂CH(CH₃)₂.

16. The compound of claim 1 wherein

is chloromethyl ketone, Z is H, R₂ is the proline side chain —(CH₂)₃—, and R₃ is the leucine side chain —CH₂CH(CH₃)₂.

17. The compound of claim 1 wherein

is chloromethyl ketone, Z is H, R₂ is the serine side chain —CH₂OH and R₃ is the asparagine side chain —CH₂CONH₂.

18. The compound of claim 1 wherein

is chloromethyl ketone, Z is H, R₂ is the threonine side chain —CHOH— CH₃, and R₃ is the aspartic acid side chain —CH₂COO⁻.

19. The compound of claim 1 wherein

is chloromethyl ketone, Z is H, R₂ is the threonine side chain —CHOH— —CH₃ and R₃ is the histidine side chain

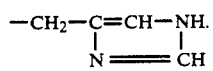

20. A compound of claim having a [TF:VII/VIIa] inhibitory potency $K_i5$ of at least 2.0 MU or $K_i50$ of less than 300 μM.

21. A composition for inhibiting specific proteolytic activity of [TF:VII/VIIa] in an animal or human comprising a composition according to claim 1 or a pharmaceutically acceptable salt thereof, and a pharmaceutically acceptable carrier.

22. A composition for inhibiting specific proteolytic activity of [TF:VII/VIIa] in an animal or human comprising a composition according to claim 2 or a pharmaceutically acceptable salt thereof, and a pharmaceutically acceptable carrier.

23. A composition for inhibiting specific proteolytic activity of [TF:VII/VIIa] in an animal or human comprising a composition according to claim 3 or a pharmaceutically acceptable salt thereof, and a pharmaceutically acceptable carrier.

24. A composition for inhibiting specific proteolytic activity of [TF:VII/VIIa] in an animal or human comprising a composition according to claim 4 or a pharmaceutically acceptable salt thereof, and a pharmaceutically acceptable carrier.

25. A composition for inhibiting specific proteolytic activity of [TF:VII/VIIa] in an animal or human comprising a composition according to claim 5 or a pharmaceutically acceptable salt thereof, and a pharmaceutically acceptable carrier.

26. A composition for inhibiting specific proteolytic activity of [TF:VII/VIIa] in an animal or human comprising a composition according to claim 6 or a pharmaceutically acceptable salt thereof, and a pharmaceutically acceptable carrier.

27. A composition for inhibiting specific proteolytic activity of [TF:VII/VIIa] in an animal or human comprising a composition according to claim 7 or a pharmaceutically acceptable salt thereof, and a pharmaceutically acceptable carrier.

28. A composition for inhibiting specific proteolytic activity of [TF:VII/VIIa] in an animal or human comprising a composition according to claim 8 or a pharmaceutically acceptable salt thereof, and a pharmaceutically acceptable carrier.

29. A composition for inhibiting specific proteolytic activity of [TF:VII/VIIa] in an animal or human comprising a composition according to claim 9 or a pharmaceutically acceptable salt thereof, and a pharmaceutically acceptable carrier.

30. A composition for inhibiting specific proteolytic activity of [TF:VII/VIIa] in an animal or human comprising a composition according to claim 10 or a pharmaceutically acceptable salt thereof, and a pharmaceutically acceptable carrier.

31. A composition for inhibiting specific proteolytic activity of [TF:VII/VIIa] in an animal or human comprising a composition according to claim 11 or a pharmaceutically acceptable salt thereof, and a pharmaceutically acceptable carrier.

32. A composition for inhibiting specific proteolytic activity of [TF:VII/VIIa] in an animal or human comprising a composition according to claim 12 or a pharmaceutically acceptable salt thereof, and a pharmaceutically acceptable carrier.

33. A composition for inhibiting specific proteolytic activity of [TF:VII/VIIa] in an animal or human comprising a composition according to claim 13 or a pharmaceutically acceptable salt thereof, and a pharmaceutically acceptable carrier.

34. A composition for inhibiting specific proteolytic activity of [TF:VII/VIIa] in an animal or human comprising a composition according to claim 14 or a pharmaceutically acceptable salt thereof, and a pharmaceutically acceptable carrier.

35. A composition for inhibiting specific proteolytic activity of [TF:VII/VIIa] in an animal or human comprising a composition according to claim 15 or a pharmaceutically acceptable salt thereof, and a pharmaceutically acceptable carrier.

36. A composition for inhibiting specific proteolytic activity of [TF:VII/VIIa] in an animal or human comprising a composition according to claim 16 or a pharmaceutically acceptable salt thereof, and a pharmaceutically acceptable carrier.

37. A composition for inhibiting specific proteolytic activity of [TF:VII/VIIa] in an animal or human comprising a composition according to claim 17 or a pharmaceutically acceptable salt thereof, and a pharmaceutically acceptable carrier.

38. A composition for inhibiting specific proteolytic activity of [TF:VII/VIIa] in an animal or human comprising a composition according to claim 18 or a pharmaceutically acceptable salt thereof, and a pharmaceutically acceptable carrier.

39. A composition for inhibiting specific proteolytic activity of [TF:VII/VIIa] in an animal or human comprising a composition according to claim 19 or a pharmaceutically acceptable salt thereof, and a pharmaceutically acceptable carrier.

40. A method for inhibiting thrombus formation, intravascular coagulation or related disorders in an animal or human comprising the step of administering to said animal or human a pharmacologically effective dose of a compound according to claim 1.

41. A method for inhibiting thrombus formation, intravascular coagulation or related disorders in an animal or human comprising the step of administering to said animal or human a pharmacologically effective dose of a compound according to claim 2.

42. A method for inhibiting thrombus formation, intravascular coagulation or related disorders in an animal or human comprising the step of administering to said animal or human a pharmacologically effective dose of a compound according to claim 3.

43. A method for inhibiting thrombus formation, intravascular coagulation or related disorders in an animal or human comprising the step of administering to said animal or human a pharmacologically effective dose of a compound according to claim 4.

44. A method for inhibiting thrombus formation, intravascular coagulation or related disorders in an animal or human comprising the step of administering to said animal or human a pharmacologically effective dose of a compound according to claim 5.

45. A method for inhibiting thrombus formation, intravascular coagulation or related disorders in an animal or human comprising the step of administering to said animal or human a pharmacologically effective dose of a compound according to claim 6.

46. A method for inhibiting thrombus formation, intravascular coagulation or related disorders in an animal or human comprising the step of administering to said animal or human a pharmacologically effective dose of a compound according to claim 7.

47. A method for inhibiting thrombus formation, intravascular coagulation or related disorders in an animal or human comprising the step of administering to said animal or human a pharmacologically effective dose of a compound according to claim 8.

48. A method for inhibiting thrombus formation, intravascular coagulation or related disorders in an animal or human comprising the step of administering to said animal or human a pharmacologically effective dose of a compound according to claim 9.

49. A method for inhibiting thrombus formation, intravascular coagulation or related disorders in an animal or human comprising the step of administering to said animal or human a pharmacologically effective dose of a compound according to claim 10.

50. A method for inhibiting thrombus formation, intravascular coagulation or related disorders in an animal or human comprising the step of administering to said animal or human a pharmacologically effective dose of a compound according to claim 11.

51. A method for inhibiting thrombus formation, intravascular coagulation or related disorders in an animal or human comprising the step of administering to said animal or human a pharmacologically effective dose of a compound according to claim 12.

52. A method for inhibiting thrombus formation, intravascular coagulation or related disorders in an animal or human comprising the step of administering to said animal or human a pharmacologically effective dose of a compound according to claim 13.

53. A method for inhibiting thrombus formation, intravascular coagulation or related disorders in an animal or human comprising the step of administering to said animal or human a pharmacologically effective dose of a compound according to claim 14.

54. A method for inhibiting thrombus formation, intravascular coagulation or related disorders in an animal or human comprising the step of administering to said animal or human a pharmacologically effective dose of a compound according to claim 15.

55. A method for inhibiting thrombus formation, intravascular coagulation or related disorders in an animal or human comprising the step of administering to said animal or human a pharmacologically effective dose of a compound according to claim 16.

56. A method for inhibiting thrombus formation, intravascular coagulation or related disorders in an animal comprising the step of administering to said animal or human a pharmacologically effective dose of a compound according to claim 17.

57. A method for inhibiting thrombus formation, intravascular coagulation or related disorders in an animal or human comprising the step of administering to said animal or human a pharmacologically effective dose of a compound according to claim 18.

58. A method for inhibiting thrombus formation, intravascular coagulation or related disorders in an animal or human comprising the step of administering to said animal or human a pharmacologically effective dose of a compound according to claim 19.

* * * * *